United States Patent [19]

Crea

[11] 4,310,662
[45] Jan. 12, 1982

[54] NUCLEOSIDIC PHOSPHORYLATING AGENT AND METHODS

[75] Inventor: Roberto Crea, Burlingame, Calif.

[73] Assignee: Genentech, Inc., San Francisco, Calif.

[21] Appl. No.: 107,055

[22] Filed: Dec. 26, 1979

[51] Int. Cl.³ .................... C07H 19/10; C07H 19/16; C07H 21/00
[52] U.S. Cl. ....................................... 536/27; 536/22; 536/28; 536/29
[58] Field of Search ...................... 536/26, 28, 29, 27, 536/22

[56] References Cited

PUBLICATIONS

Chemical Abstracts, vol. 90, p. 148056, Crea, R., et al., No. 148062, "Chemical Synthesis of Genes for Human Insulin," Proc. Natl. Acad. Sci. U.S.A., 75(12), 5765–5769, 1978.
Itakura, K., et al., Can. J. Chem., vol. 51, pp. 3649–3651, 1973.
Crea et al., Proceediungs of The National Academy of Science, vol. 75, pp. 5765–5769, 1978.

Primary Examiner—Johnnie R. Brown
Assistant Examiner—Blondel Hazel

[57] ABSTRACT

Compounds of the formula

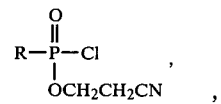

where R is a base labile substituted-phenyloxy protecting group, are useful as phosphorylating reagents in the synthesis of oligonucleotides by a phosphotriester method. Such compounds are made by the reaction of β-cyanoethanol and a corresponding R-phosphorodichloridate. A method of phosphorylating involves reacting such compounds, in the presence of base, with a nucleoside or a polynucleotide having a free 3' hydroxyl group, having the 5'—O position protected by an organic group labile in acidic medium and having any phosphotriester linking groups protected by an organic group labile in strong basic medium.

11 Claims, No Drawings

NUCLEOSIDIC PHOSPHORYLATING AGENT AND METHODS

BACKGROUND OF THE INVENTION

With the coming of age of recombinant DNA technology attention has increasingly been focused on the synthesis of oligonucleotides for various purposes, e.g., as hybridization probes for use in locating complementary DNA made by reverse transcription from purified messenger RNA, as primers in the controlled conversion of single to double-stranded DNA, as plasmidic control regions useful in the bacterial expression of useful proteins, as "linkers" for interpolating heterologous DNA into plasmids, as genes encoding useful proteins that themselves may be bacterially expressed, and so on. In each such case DNA fragments have hitherto been assembled by condensation of nucleotides or oligonucleotides according to a sequential plan dictated by the nucleotide sequence of the desired end product. As one example, the known amino acid sequence of the useful compound somatostatin has permitted design and synthesis of a corresponding gene, which could then be inserted in a bacterial plasmid so as to permit bacterial production of the protein encoded. K. Itakura, et al., Science 198, 1056–1063 (1977).

The construction of oligonucleotides entails phosphorylation of a nucleosidic moiety to form the corresponding 3'-phosphate, which is then condensed with a further, suitably protected nucleosidic moiety to yield a di- or polynucleotide in which the original nucleosidic moieties are linked by a phosphodiester bridge. In the so-called "triester" method the third functionality of the phosphate is protected prior to the condensation reaction to prevent undue side reactions and to neutralize charge so as to permit silica gel chromatography techniques in product purification and recovery. See, e.g., K. Itakura et al, Can. J. Chem. 51, 3649–3651 (1973) and the somatostatin work previously referred to. A typical series of steps in oligonucleotide constructions typical of past triester practice may be represented as follows, "B" being the characteristic base moiety of the nucleoside involved, X a protecting group for the 5'—OH, and R, e.g., p-chlorophenoxy:

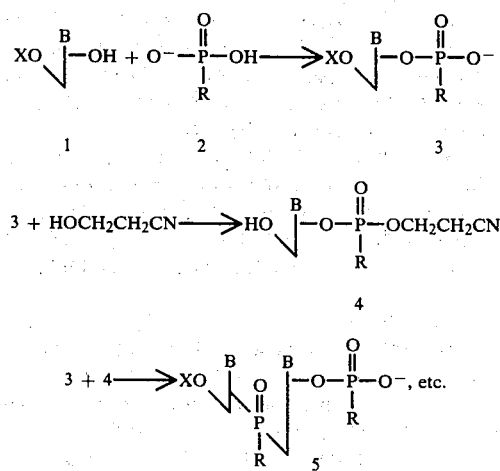

In the foregoing scheme the possibility exists in the first reaction of byproduct formation owing to e.g., multiple phosphorylation. More to the point, the intermediate product 3 is charged, so that the β-cyanoethanol reactant in the following step must be used in considerable (e.g., 5X) excess if the presence of a polar nucleotidic moiety is to be avoided when product 4 comes to be purified and, of course, workup and purification of 4 is in any event complicated by the excess remaining. Finally, end product 5 is itself charged, and hence cannot be purified in silica gel chromatography, an otherwise highly convenient tool.

A need has accordingly existed for improved means of DNA and other oligonucleotide synthesis, so as to diminish recovery losses, otherwise enhance yields, and to permit more rapid synthesis of key materials in health-related and other fields.

BRIEF SUMMARY OF THE INVENTION

The present invention provides as a novel phosphorylating compound the material

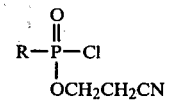

where R is a base labile phenyloxy protecting group. As a single step phosphyorylating reagent, the compound permits phosphorylation and condensation to go forward without workup of intermediate product or the need for an interposed β-cyanoethylation step, and yields as end product a neutral oligonucleotide which admits of facile purification and recovery in high yields. Using the new reagent, it proved possible in just three months to produce 29 different oligodeoxyribonucleotides to build genes for human insulin, R. Crea et al, Prod. Nat'l Acad. Sci. USA 75, 5765–5769, Dec. 1978, which could then occasion bacterial expression of that precious substance, D. Goeddel et al, Proc. Nat'l. Acad. Sci. 76, 106–110 Jan. 1979; and subsequently to construct 12 further oligonucleotides to supply synthetic components of a gene used successfully in the bacterial production of human growth hormone, D. Goeddel et al, Nature 281, 544–548 (Oct. 1979). These and the other publications referred to herein are incorporated by reference to illustrate, variously, the background and advantages of the invention. The manner in which the foregoing and other objects and advantages of the invention are attained will further appear from the detailed description which follows.

DETAILED DESCRIPTION OF THE INVENTION

The compounds of the invention may be made by reaction of β-cyanoethanol and R-phosphorodichloridate in ether/triethylamine, i.e.,

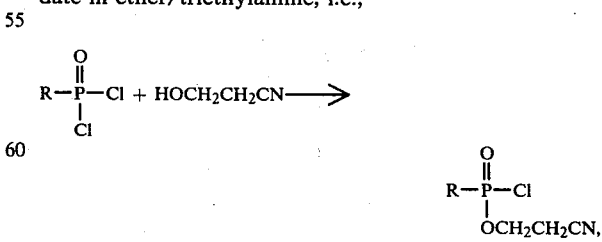

where R is a base labile phenyloxy protecting group, e.g., p-chlorophenyloxy, o-chlorophenyloxy, 2,4-dichlorophenyloxy, p-nitrophenyloxy, p-methoxyphenyloxy, etc.

Use of the compounds in DNA synthesis may be represented by the following reaction scheme in which the preferred embodiment of the invention, p-chlorophenyl-2-cyanoethylphosphorochloridate is employed:

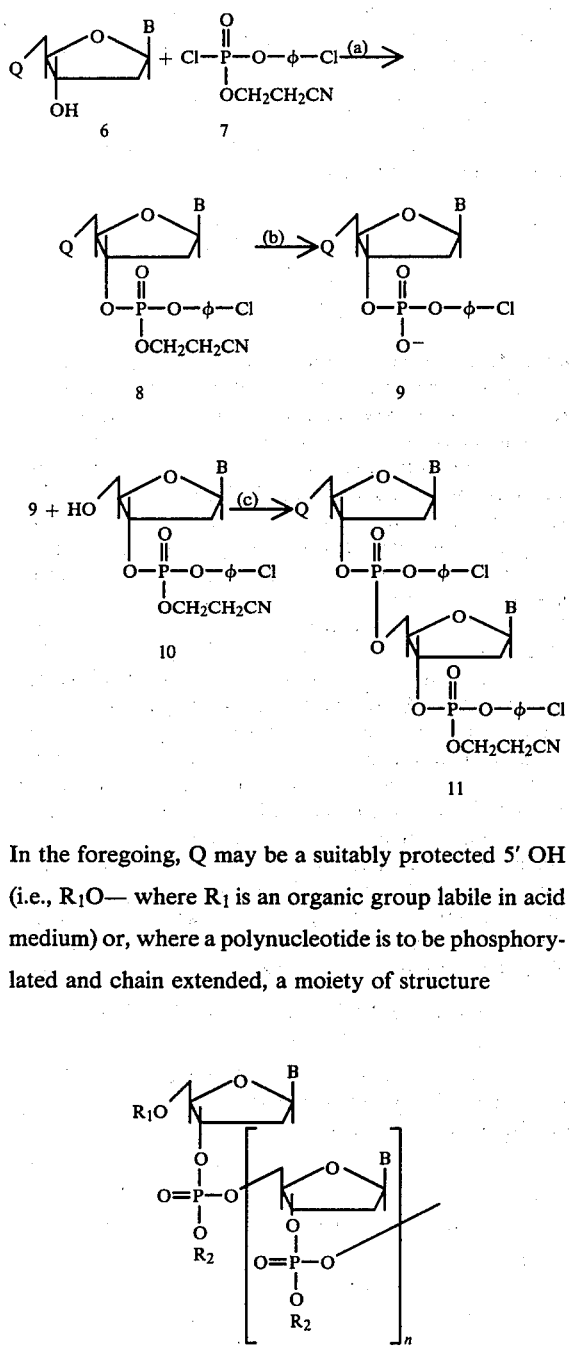

In the foregoing, Q may be a suitably protected 5' OH (i.e., $R_1O$— where $R_1$ is an organic group labile in acid medium) or, where a polynucleotide is to be phosphorylated and chain extended, a moiety of structure where n is zero or an integer from 1 to about 18.

In like fashion, the reactant 10 may alternatively be a polynucleotide, e.g.,

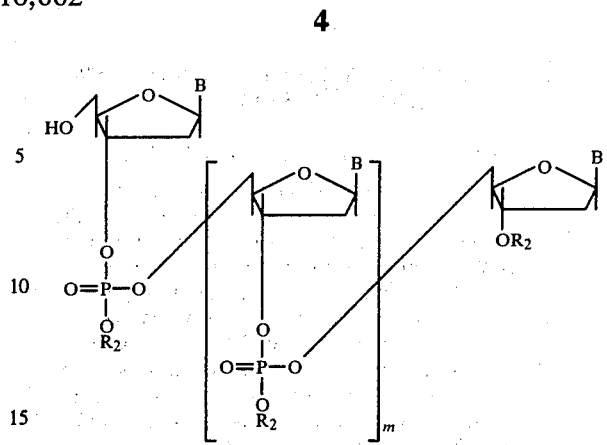

where m is zero or an integer so chosen that the sum of n and m is not greater than about 17. The group B in any case may be the same or different and is selected from the group consisting of adenyl, thymyl, guanyl and cytosyl. $R_2$ is a protecting group that is labile in basic medium.

The phosphorylation reaction (a) is conducted in a suitable solvent, e.g., acetonitrile, in the presence of base to neutralize hydrogen chloride formed as by-product, thus driving the reaction toward completion. A preferred basic medium for this purpose is 1-methylimidazole, which also serves to activate the phosphorochloridate. Temperature is non-critical and all reactions depicted may be run at, e.g., room temperature, although the phosphorylation reaction is preferably run at somewhat reduced temperature, e.g., at or about 0° centigrade. Reaction (b) removes the cyanoethyl moiety by base-catalyzed β-elimination preferably in a pyridine/triethylamine/water system (3:1:1 vol/vol). Condensation reaction (c) employs a coupling agent in excess (e.g., 3–4 equivalents), preferably 2,4,6-triisopropylbenzenesulfonyl tetrazolide and is performed in pyridine, preferably with an excess (e.g., 1.5 equivalents or more) of the charged reactant 9. Because the intended product 11 is relatively neutral the excess of the charged reactant 9 may be removed by silica gel chromatography. Thus, as an example, the final reaction mixture is passed through a silica gel column washed first with $CHCl_3$ to elute side products and coupling agent, then with $CHCl_3/MeOH$ (95:5 vol/vol) to elute the fully protected oligomer, leaving the charged reactant behind in the column.

Among the many acid labile protecting groups useful in such condensation reactions may be mentioned, e.g., tetrahydropyrenyl, 1-methoxycyclohexyl, 4-monomethoxytrityl and, most preferably, 4,4'-dimethoxytrityl, which latter may be removed in mild acid medium, e.g., 2% benzenesulfonic acid.

The group $R_2$ is removable in strong basic medium, e.g., concentrated ammonia or NaOH, and may be, e.g., orthochlorophenyl, 2, 4-dichlorophenyl, parachlorophenyl, paranitrophenyl, etc. It is accordingly unaffected by the β-elimination reaction which removes the cyanoethyl moiety, the latter being carried out in weak basic medium, i.e., from near-neutrality to about pH 9.

In the example that follows, the method of forming the most preferred embodiment of the invention is illustrated in greater detail.

EXAMPLE

Synthesis of p-chlorophenyl-2-cyanoethylphosphorochloridate.

A solution of freshly distilled triethylamine (14 ml, 0.1 mole) in ether (100 ml) was added, dropwise and under magnetical stirring, to a chilled solution (ice water bath) of p-chlorophenyl phosphorodichloridate (24.5 g. 0.1 mole) and 2-cyanoethanol (7 ml, 0.1 mole) in ether (300 ml). After complete addition of the base, the solution was stirred for one hour at room temperature and then quickly filtrated. The ether was evaporated off and the product recovered as an oil. Appropriate choice of the starting phosphorodichloridate yields the other fully protected phosphorylating agents of the invention, by a like procedure.

I claim:

1. A method of phosphorylating a moiety of structure

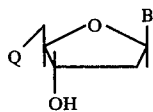

wherein B is adenyl, thymyl, guanyl or cytosyl and Q is selected from the group consisting of $R_1O$-, and

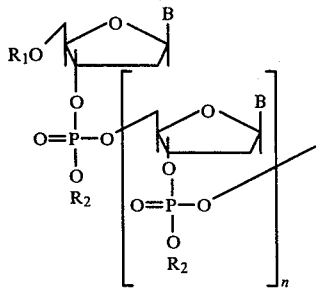

wherein n is zero or an integer from 1 to about 18, $R_1$ is an organic group labile in acidic medium and $R_2$ is an organic group labile in basic medium which comprises reacting said moiety with a phosphorylating reagent of structure

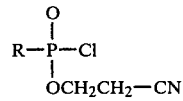

wherein R is a base labile phenyloxy protecting group, in the presence of a weak base to form the product

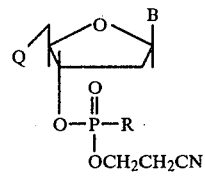

2. A method according to claim 1, which further comprises reacting said product in the presence of base to remove the cyanothyl group and to form the compound

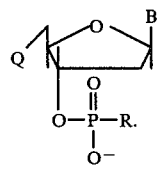

3. A method according to claim 2, wherein $R_1$ is an organic protecting group labile in acidic medium and $R_2$ is an organic protecting group labile in basic medium.

4. A method according to claim 2, wherein R is selected from the group consisting of p-chlorophenyloxy, o-chlorophenyloxy, 2,4-dichlorophenyloxy, p-nitrophenyloxy and p-methoxyphenyloxy groups.

5. A method according to claim 2, wherein R is p-chlorophenyloxy.

6. A method according to claim 2, wherein $R_2$ is a phenyl group labile in basic medium.

7. A method according in claim 2, wherein $R_2$ is selected from the group consisting of p-chlorophenyl, o-chlorophenyl, 2,4-dichlorophenyl, p-nitrophenyl, and p-thiophenyl groups.

8. A method according to claim 2, wherein $R_2$ is p-chlorophenyl.

9. A method according to claim 2, wherein $R_1$ is a trityl group labile in acidic medium.

10. A method according to claim 2, wherein $R_1$ is 4,4'-dimethoxytrityl.

11. A method according to claim 2, wherein $R_1$ is selected from the group consisting of 4-monomethoxytrityl and 4,4'-dimethoxytrityl groups.

* * * * *